(12) United States Patent
Ahn et al.

(10) Patent No.: US 7,037,313 B2
(45) Date of Patent: May 2, 2006

(54) APPARATUS FOR STRIPPING FIBRIN FROM A CATHETER

(75) Inventors: Jiyong Ahn, Yonkers, NY (US); Paul R. Gianneschi, Snellville, CA (US); Steven M. Hvozda, Atlanta, GA (US)

(73) Assignee: Fibrex, LLC, Snellville, GA (US)

( * ) Notice: Subject to any disclaimer, the term of this patent is extended or adjusted under 35 U.S.C. 154(b) by 505 days.

(21) Appl. No.: 10/100,027

(22) Filed: Mar. 19, 2002

(65) Prior Publication Data

US 2003/0181876 A1   Sep. 25, 2003

(51) Int. Cl.
*A61B 17/24* (2006.01)

(52) U.S. Cl. ...................................... 606/113

(58) Field of Classification Search ........ 606/113–114, 606/110, 107, 106, 108, 222, 224, 139, 144, 606/119, 128; 604/52; 128/898
See application file for complete search history.

(56) References Cited

U.S. PATENT DOCUMENTS

| 5,556,380 A | 9/1996 | Ridinger et al. ............ 640/52 |
| 5,558,643 A | 9/1996 | Samson et al. |
| 5,643,281 A * | 7/1997 | Suhocki et al. ............. 606/113 |
| 5,800,444 A | 9/1998 | Ridinger et al. ............ 606/113 |
| 6,027,516 A | 2/2000 | Kolobow et al. |
| 6,027,576 A | 2/2000 | Schrey et al. |
| 6,402,771 B1 | 6/2002 | Palmer et al. |
| 6,416,545 B1 | 7/2002 | Mikus et al. |
| 6,491,680 B1 * | 12/2002 | Batiste ....................... 604/523 |
| 6,500,182 B1 | 12/2002 | Foster |
| 6,562,031 B1 | 5/2003 | Chandrasekaran et al. |
| 6,575,967 B1 * | 6/2003 | Leveen et al. ................ 606/41 |

* cited by examiner

*Primary Examiner*—Vy Bui
(74) *Attorney, Agent, or Firm*—Welsh & Flaxman LLC (57) ABSTRACT

An apparatus for the removal of build-up about an implanted catheter having an interior surface, an exterior surface and an open free end positioned within an individual's vascular system. The apparatus includes a delivery assembly storing a stripping coil. The delivery assembly includes a guide structure for guiding the stripping coil through the catheter to the free end of the catheter. The stripping coil is formed of a shape memory or super-elastic material, wherein the stripping coil is preformed to assume a shape wrapping about the outer surface of the catheter in a manner providing for the stripping of build-up from the outer surface of the catheter when the stripping coil is moved relative to the catheter.

17 Claims, 6 Drawing Sheets

APPARATUS FOR STRIPPING FIBRIN FROM A CATHETER

BACKGROUND OF THE INVENTION

1. Field of the Invention

The invention relates to a method and apparatus for stripping fibrin and thrombus build-up from a catheter. More specifically, the invention relates to a method and apparatus employing a shape memory or super-elastic stripping coil to strip fibrin build-up from both the interior and exterior of a dialysis catheter.

2. Description of the Prior Art

The use of long and short term, implanted catheters has become commonplace in the practice of medicine. These catheters are commonly formed of biocompatible plastic materials and are implanted to relieve various symptoms and/or to assist in medical procedures. For example, dialysis catheters are commonly implanted to facilitate simplified dialysis procedures for those patients requiring such assistance.

The use of these catheters is not without problems. For example, these biocompatible plastic catheters are susceptible to the formation of deposits of fibrin and platelets, referred to as fibrin sheaths. Such fibrin sheaths commonly form along the open free end of an implanted dialysis catheter, covering both the exterior and interior surfaces of the catheter.

As those skilled in the art appreciate, the build-up of such fibrin sheaths is undesirable and can cause catheter dysfunction. Once the presence and extent of the fibrin sheath have been identified, the physician must take the necessary steps to remove the sheath from the implanted catheter. While it is conceivable that the implanted catheter may be removed and replaced surgically, it is more desirable for the fibrin sheath to be removed without surgical removal of the implanted catheter.

Various techniques have been developed for the removal of such sheaths; however, no prior technique has been able to effectively remove the fibrin sheath from the outer surface of the catheter in a convenient and reliable manner causing minimal trauma to the patient. The present invention provides an apparatus and method overcoming the shortcomings of these prior art devices.

SUMMARY OF THE INVENTION

It is, therefore, an object of the present invention to provide an apparatus for the removal of build-up about an implanted catheter having an interior surface, an exterior surface and an open free end positioned within an individual's vascular system. The apparatus includes a delivery assembly storing a stripping coil. The delivery assembly includes a guide structure for guiding the stripping coil through the catheter to the free end of the catheter. The stripping coil is formed of a shape memory or super-elastic material, wherein the stripping coil is preformed to assume a shape wrapping about the outer surface of the catheter in a manner providing for the stripping of build-up from the outer surface of the catheter when the stripping coil is moved relative to the catheter.

It is also an object of the present invention to provide an apparatus wherein the stripping coil is formed of Nitinol.

It is another object of the present invention to provide an apparatus wherein the stripping coil is preformed to assume a helical shape.

It is a further object of the present invention to provide an apparatus wherein the delivery assembly includes means for rotating the stripping coil relative to the catheter so as to facilitate removal of build-up from the exterior surface of the catheter.

It is also an object of the present invention to provide a method for the removal of build-up about an implanted catheter. The method is achieved by preforming a stripping coil, composed of a shape memory material, to assume a shape wrapping about the exterior surface of the catheter, coupling a delivery system to an accessible portion of the catheter; guiding the stripping coil to the open free end of the catheter, releasing the stripping coil such that it assumes its preformed shape wrapping about the exterior surface of the catheter, and moving the stripping coil relative to the catheter such that the stripping coil disengages and removes build-up along the exterior surface of the catheter.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiments of the present invention are disclosed herein. It should be understood, however, that the disclosed embodiments are merely exemplary of the invention, which maybe embodied in various forms. Therefore, the details disclosed herein are not to be interpreted as limiting, but merely as the basis for the claims and as a basis for teaching one skilled in the art how to make and/or use the invention.

With reference to FIGS. 1 to 6, an apparatus 110 for the removal of thrombus build-up in and around an implanted catheter 112 is disclosed. The apparatus 110 is particularly suited for removing fibrin build-up from the exterior surface 114 of a dialysis catheter 112 having an interior surface 116, an exterior surface 114 and an open free end 118 positioned within an individual's vascular system. While the present apparatus is described below for use in the stripping of fibrin from a dialysis catheter, it should be understood that the present stripping apparatus maybe used for a variety of applications within the scope of the present invention, such as, removal of any type of buildup. In addition, the apparatus disclosed herein is described with reference to its use in a dual lumen catheter. However, many other catheter structures are known to those skilled in the art and it is contemplated that the present apparatus maybe used with catheters of various configurations within the spirit of the present invention.

Figure 1:
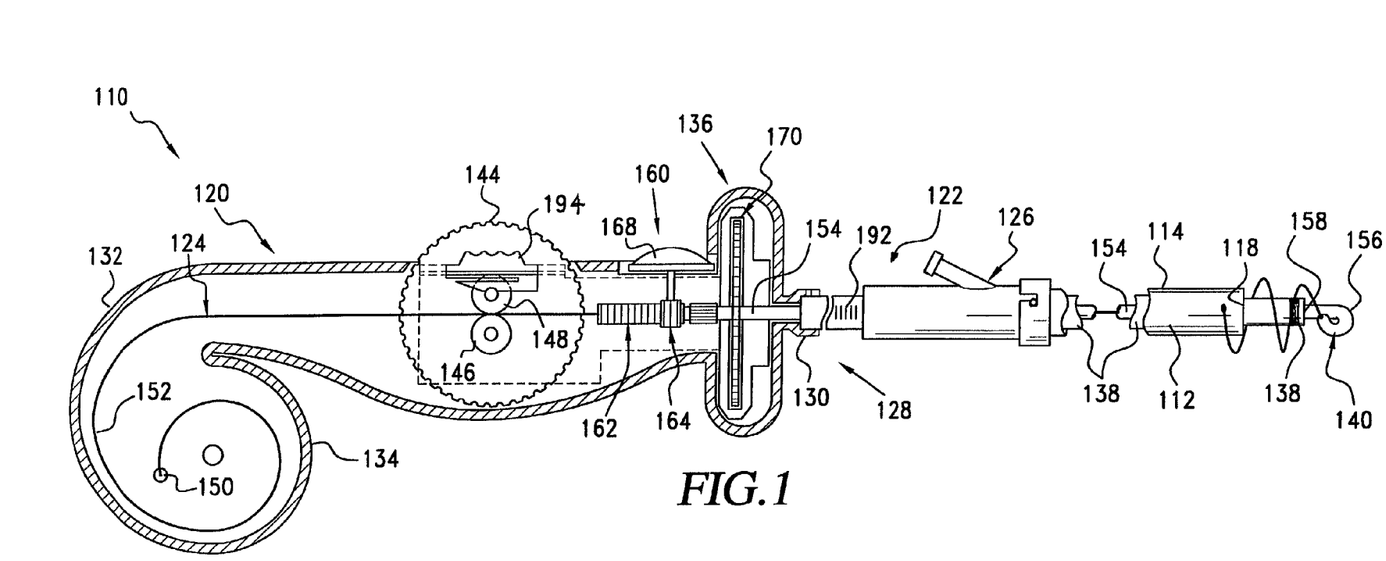
FIG. 1 is a side view of the present apparatus for the removal of thrombus build-up in and around an implanted catheter.

In accordance with a preferred embodiment of the present invention, the apparatus 110 generally includes a delivery assembly 120, a stripping coil 124 formed of a shape memory material and a guide structure 122 for guiding the stripping coil 124 through the catheter 112 and to the free end 118 of the catheter 112. The stripping coil 124 is preformed to assume a shape wrapping about the exterior surface 114 of the catheter 112 in a manner providing for the stripping of build-up from the exterior surface 114 of the catheter 112 when the stripping coil 124 is moved relative to the catheter 112.

With reference to FIG. 1, and in accordance with a preferred embodiment of the present invention, the delivery assembly 120 is adapted for selectively coupling to a luer connector 126 secured to the venous lumen of a traditional dialysis catheter 112. For example, and in accordance with a preferred embodiment of the present invention, the proximal end 128 of the delivery assembly 120 includes a coupling member 130 shaped and dimensioned for selective attachment to a Touhy Borst Adapter, although those skilled in the art will appreciate the wide variety of connections which may be utilized within the spirit of the present invention.

The delivery assembly 120 includes a housing 132 having a first end 134 and a second end 136. As mentioned above, the second end 136 includes a coupling member 130. An outer catheter 138 is further secured to the second end 136 of the housing 132 and extends away from the housing 132 defining a lumen through which the stripping coil 124 and the guide curve 140 are passed as they are positioned adjacent the open free end 118 of the dialysis catheter 112 in a manner which will be discussed below in greater detail. With this in mind, the outer catheter 138 is shaped and dimensioned to fit within the dialysis catheter 112 and extends to approximately the open free end 118 of the dialysis catheter 112. As such, the outer catheter 138 is structured to be approximately the same length as the dialysis catheter 112. In an effort to ensure proper positioning of the outer catheter 138 adjacent the free end 118 of the dialysis catheter 112, the outer catheter 138 is provided with a radiopaque marker adjacent its distal end 158 and printed markings 192. As such, a physician may readily monitor the position of the outer catheter 138 relative to the dialysis catheter 112 so as to properly position the delivery assembly 120 before attaching the coupling member 130 to the connector 126 of the dialysis catheter 112.

Figure 4:
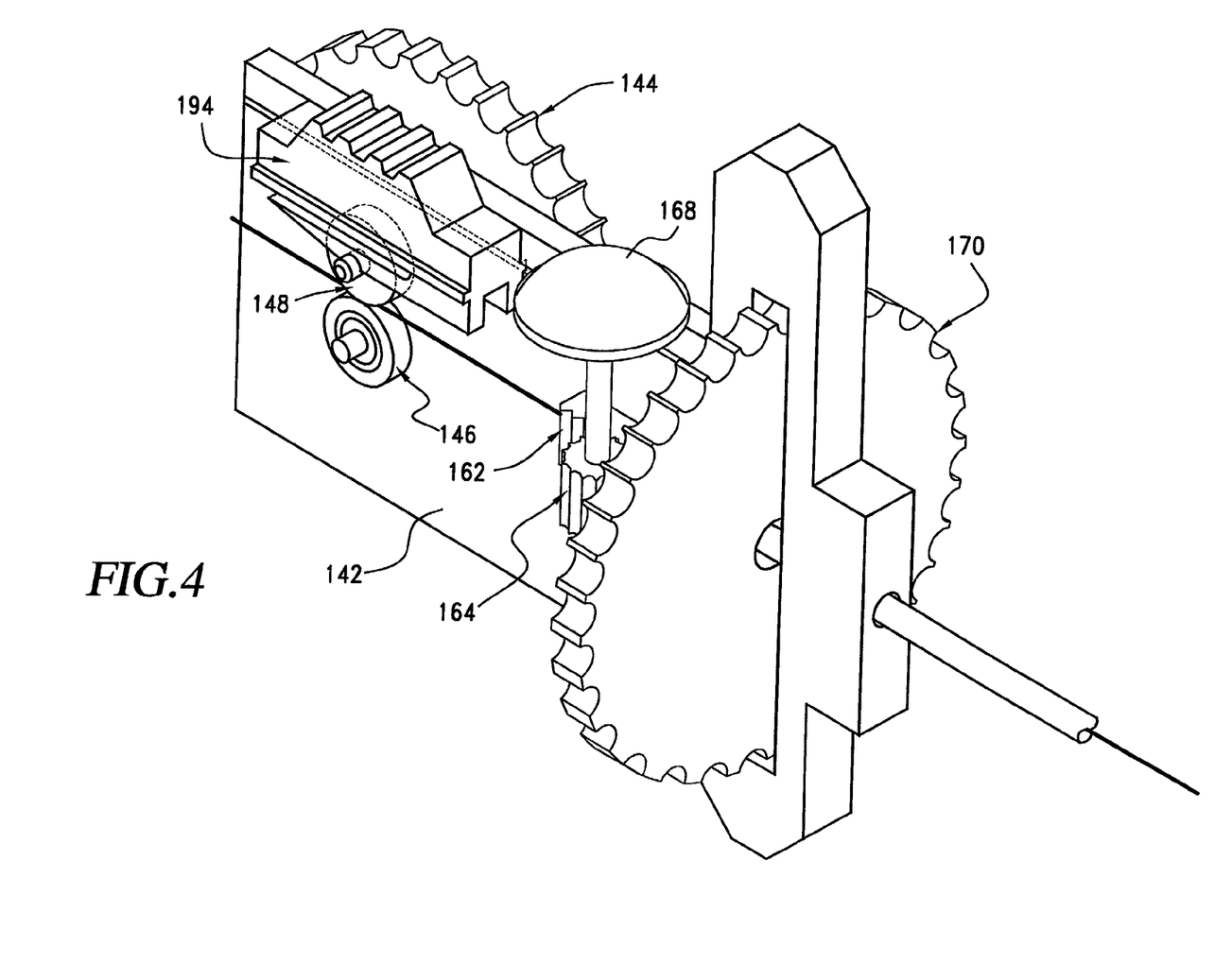
FIG. 4 is a detailed view of the drive mechanism utilized in accordance with the apparatus disclosed in FIG. 1.

The housing 132 of delivery assembly 120 further provides for the controlled storage and release of the various delivery components utilized in the proper positioning of the stripping coil 124 within the dialysis catheter 112. With this in mind, and as will be better appreciated based upon the following disclosure, the housing 132 stores a capstan drive 142 capable of inserting an indefinite length of stripping coil 124 within the dialysis catheter. The capstan drive 142 includes a thumb wheel 144 linked to a drive wheel 146 and driven wheel 148 which push the stripping coil 124 forward within the system when thumb wheel 144 is rotated clockwise. Movement of the stripping coil 124 beyond the drive and driven wheels 146, 148 is facilitated by the provision of a stop member 150 at the proximal end 152 of the stripping coil 124.

An inner catheter 154 having a guide curve 140 secured at its distal end 156 is coupled within the housing 132 in a manner discussed below in greater detail. The inner catheter 154 extends within the outer catheter 138 and guides a guide curve 140 toward the distal end 158 of the outer catheter 138. In use, the guide curve 140 is moved beyond the distal end 158 of outer catheter 138 and functions to direct the stripping coil 124 as it is pushed outwardly beyond the end of the delivery assembly 120.

Movement of the guide curve 140, and the inner catheter 154, is facilitated by providing the delivery assembly 120 with a guide curve deployment assembly 160. Specifically, the guide curve deployment assembly 160 is positioned at a location distally of the capstan drive 142 and provides for the controlled deployment of the guide curve 140 in a manner which will be discussed below in greater detail. The guide curve deployment assembly 160 includes rack 162 and pinion 164 to which the proximal end 166 of the inner catheter 154 is secured. Actuation of the rack 162 and pinion 164 assembly is facilitated by an advance/retract knob 168 accessible to a user along the upper portion of the housing 132. Rotation of the knob 168 selectively advances or retracts the inner catheter 154 between a deployed position within the outer catheter 138 and a storage position within the delivery assembly 120. While rotation is contemplated in accordance with a preferred embodiment of the present invention, other movements may be utilized without departing from the spirit of the present invention.

Figure 2:
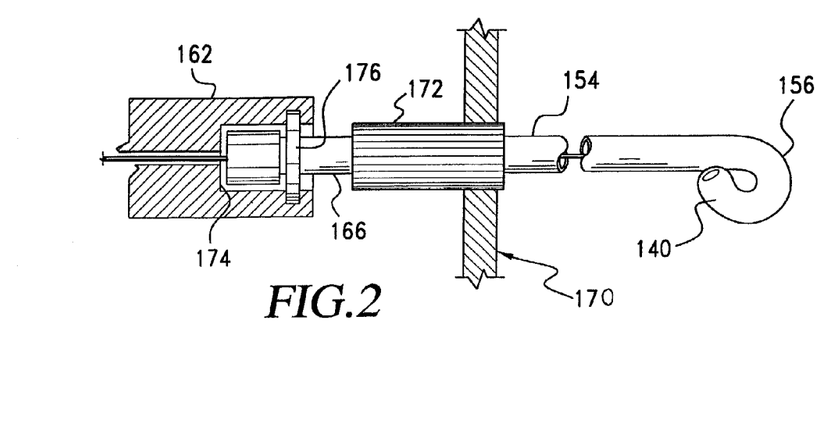
FIG. 2 is a detailed cross-sectional view of the inner catheter attachment within the housing of the apparatus disclosed in FIG. 1.

As will be discussed in greater detail below, it is necessary to rotate the stripping coil 124 to achieve removal of fibrin in accordance with the present invention. With this in mind, the delivery assembly 120 is further provided with a rotation wheel assembly 170 designed to provide for the controlled and selective rotation of the stripping coil 124. Specifically, the rotation wheel assembly 170 is positioned beyond the capstan drive 142 and the guide curve deployment assembly 160 at a location adjacent the exit point for the housing 132. The rotation wheel assembly 170 is statically coupled to a spline 172 positioned adjacent the proximal end 166 of the inner catheter 154, while the proximal end 166 of the inner catheter 154 is coupled to the guide curve deployment assembly 160 in a manner permitting free rotation between the inner catheter 154 and the guide curve deployment assembly 160. Specifically, the proximal end 166 of the inner catheter 154 is positioned within a recess 174 formed in the rack 162 and is retained therein by a retaining ring 176 encircling the recess 174 in which the proximal end 166 of the inner catheter 154 is captured. By coupling the inner catheter 154 to the rack 162 for free rotation relative thereto, and fixedly coupling the inner catheter 154 to the rotation wheel assembly 170 for rotation therewith, an operator may selectively rotate the inner catheter 154.

As mentioned above, the stripping coil 124 is deployed via a capstan drive 142 of the delivery assembly 120. The stripping coil 124 includes a proximal end 152 which is stored within the housing 132 and includes a stop 150 to prevent excessive passage beyond the control of the capstan drive 142. In this way, a great length of the stripping coil 124 may be readily stored within the housing 132 and selectively deployed to extend beyond the inner catheter 154, outer catheter 138 and guide curve 140 such that it may freely wrap around the distal end of the dialysis catheter 112.

As briefly mentioned above, the stripping coil 124 is formed from a shape memory or super-elastic material. In accordance with a preferred embodiment of the present invention, the stripping coil 124 is formed from a Nitinol shape memory or super-elastic material, although other materials may be used without departing from the spirit of the present invention.

Figure 3:
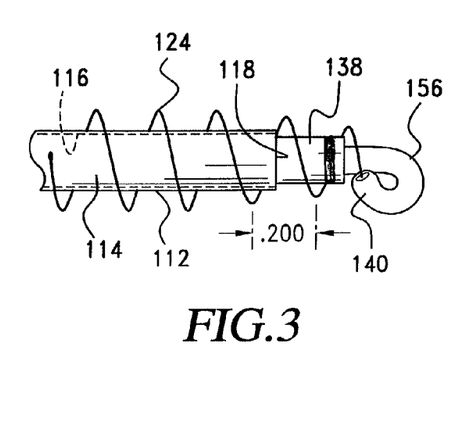
FIG. 3 is a detailed side view of the guide curve with a stripping coil deployed about a catheter.

The use of shape memory or super-elastic materials in accordance with the present invention permits the controlled deployment of the stripping coil 124. Specifically, once the stripping coil 124 is deployed adjacent to the open free end 118 of the dialysis catheter 112, its exposure to the elevated temperatures cause the stripping coil 124 to assume a predefined shape (when using shape memory materials). In accordance with a preferred embodiment of the present invention, the stripping coil 124 is preformed to extend rearwardly and assume a helical shape which wraps about the exterior surface 114 of the dialysis catheter 112. The helical shape of the stripping coil 124 contacts the exterior surface 114 of the catheter 112 and functions to dislodge fibrin build-up as it is rotated relative to the dialysis catheter 112. The helical, "cork-screw like", shape of the stripping coil 124 further functions to draw dislodged fibrin along the exterior surface 114 of the catheter 112 and mechanically brake up the fibrin allowing it to simply float away within the patient's vascular system.

In use, the present stripping apparatus 110 provides for the removal of fibrin build-up on the exterior surface 114 of the dialysis catheter 112. This removal is preferably achieved by performing the following steps in a controlled, deliberate manner. Specifically, a stripping coil 124 composed of a shape memory material is preformed to assume a shape wrapping about the exterior surface 114 of the catheter 112. This will preferably be performed during assembly of the delivery apparatus 120 in a highly controlled environment such that the stripping coil 124 assumes a desired helical shape intimately contacting the exterior surface 114 of the dialysis catheter 112 upon being exposed to elevated bodily temperatures. As mentioned above, and in accordance with a preferred embodiment of the present invention, the stripping coil 124 is preformed to assume a helical shape upon exposure to elevated bodily temperatures (when composed of a shape memory material) or upon deployment (when composed of a super-elastic material).

Figure 5:
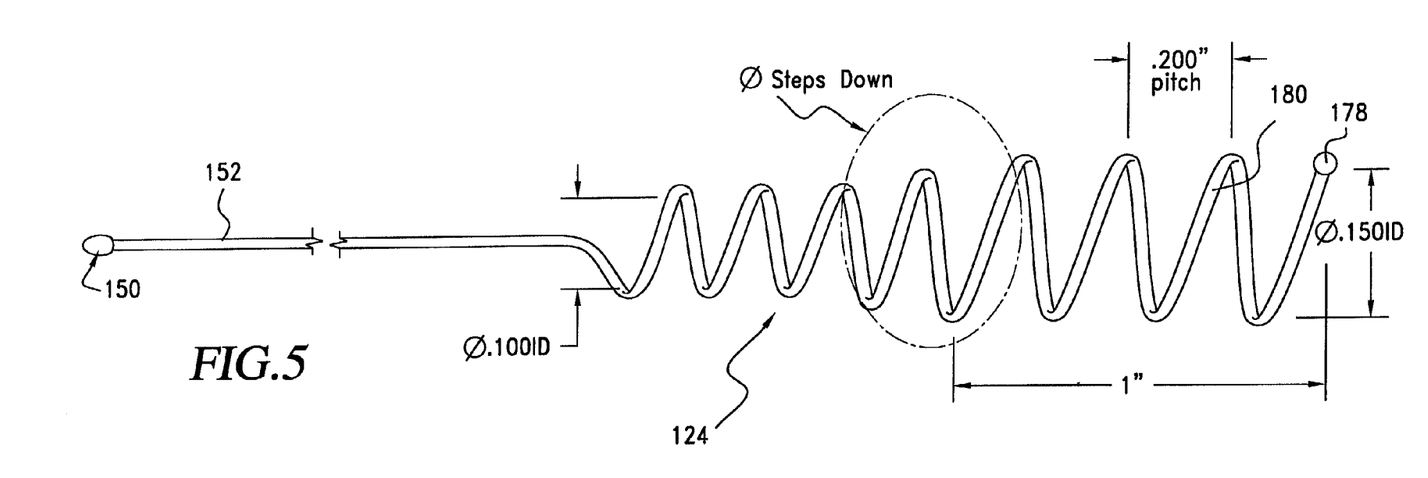
FIG. 5 is a side view of a stripping coil in accordance with the present invention.

More specifically, and with reference to FIG. 5, the stripping coil 124 is made from super-elastic shape memory or thermal shape memory responsive NiTi. The stripping coil 124 is manufactured with a step design adapted to work with multi-lumen central venous catheters. The pitch in accordance with a preferred embodiment is 0.200 inches. However, those skilled in the art will readily appreciate that the exact dimensions and construction of the coil may vary depending upon specific catheter constructions, applications and needs.

As will be better appreciated based upon the following discussion, the stripping coil 124 is formed with a left-handed helix. The left-handed helix allows the stripping coil 124 to reverse direction. Upon deployment the left-handed helix will further permit the physician to use a clockwise motion (familiar for advancing) to cause the stripping coil 124 to strip the fibrin sheath in accordance with the present invention. It is also contemplated that the stripping coil 124 will be provided with a fused/soldered/looped end 178 to minimize trauma to the patient and to function as a hard stop during retraction of the stripping coil 124. While a round cross-section is disclosed in accordance with a preferred embodiment of the present invention, other wire shapes (that is, cross-sections) may be used within the spirit of the present invention. For example, the stripping coil 124 may be round, square, diamond, rectangular, triangular, or a braid of several smaller wires. It is contemplated that these alternative configurations may provide better stripping action due to the reduced contact area with the fibrin sheath.

As briefly mentioned above, the guide curve 140 functions to control movement of the stripping coil 124 about the dialysis catheter 112. With this in mind, and with reference to FIG. 6, the structure of the guide curve 140 will now be discussed in detail. The guide curve 140 is designed to reverse the direction of the stripping coil 124 as it is deployed such that deployment of the stripping coil 124 distally within the delivery assembly 120 causes the distal end 180 of the stripping coil 124 to advance proximally and wrap about the dialysis catheter 112. With this in mind, the reversing angle of the guide curve 140 is shaped to match the pitch angle of the stripping coil 124.

Figure 6:
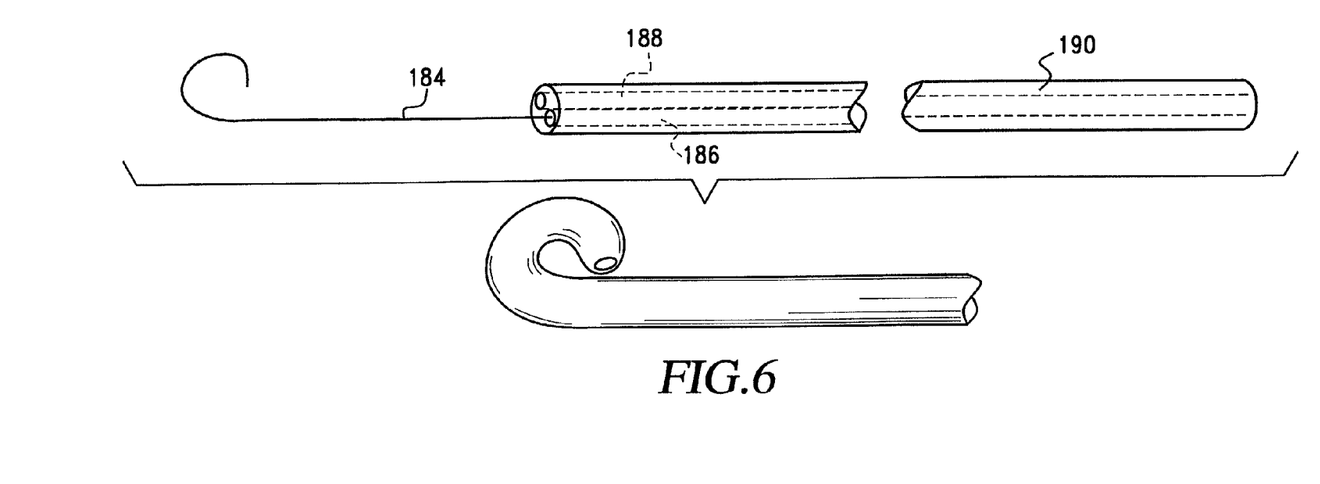
FIG. 6 is an exploded view showing assembly of the guide curve in accordance with the present invention.

The guide curve 140 is preferably constructed of a dual lumen nylon tube 182 with a thermal shape memory responsive NiTi wire 184 inserted into one of the lumens 186. The Nitinol wire 184 is glued in place within the lumen 186 using adhesive to prevent undesirable movement. A Teflon filament is inserted through the second lumen 188. During the manufacturing process, the guide curve 140 is heated so as to soften the nylon tube 182 and activate the Nitinol wire 184. This causes the nylon tube 182 to conform to the shape of the Nitinol wire 184. The Teflon filament prevents the second lumen 188 from collapsing during this heating step and is subsequently removed prior to use. The formed guide curve 140 maybe secured to a single lumen tube 190 to complete the fabrication of the complete inner catheter 154 in accordance with the present invention. While a preferred construction of the guide curve, as well as inner catheter, is described above, it is contemplated that a single lumen guide curve maybe utilized. The guide curve would be constructed of either a thermoplastic or thermoset material and could be plain or reinforced with a braid. The guide curve would be thermally set over a mandrel and would "remember" this new shape once deployed. Regardless of the guide curve construction utilized, upon deployment within the vascular system of a patient, the guide curve will assume its desired shape and return to a curved predetermined shape upon deployment.

In use, the physician, or other individual responsible for removal of fibrin, will flush the catheter lumens of the present stripping apparatus 110 with saline. The physician will then insert the outer catheter 138 into the indwelling dialysis catheter 112 to a proper depth as indicated by markings 192 along the exterior of the outer catheter 138. The delivery assembly 120 is then locked in place. As those skilled in the art will certainly appreciate, placement of the outer catheter 138 within the dialysis catheter 112 maybe verified utilizing fluoroscopy.

Once the delivery assembly 120 is locked in place, the physician will rotate the advance/retract knob 168 180° clockwise. This rotates the pinion 164 and rack 162 gears to advance the inner catheter 154, and guide curve 140, within the outer catheter 138 and dialysis catheter 112 a sufficient distance to deploy the guide curve 140 distally beyond the outer catheter 138. Once the guide curve 140 is fully deployed, the physician slides the capstan slide lock 194 to lock the capstan driven wheel 148 against the capstan drive wheel 146, pinching the stripping coil 124 between the capstan driven wheel 148 and the capstan drive wheel 146.

The physician then rotates the thumb wheel 144 clockwise to deploy the stripping coil 124. As the stripping coil 124 enters the vascular system of the patient it will be guided by the guide curve 140 and begin wrapping around the dialysis catheter 112. If in accordance with a desired use of the present invention, a body temperature responsive Nitinol stripping coil 124 is utilized, it will remember its shape and begin wrapping around the dialysis catheter 112 upon exposure to the elevated body temperature. If a superelastic Nitinol stripping coil is utilized in accordance with a preferred embodiment of the present invention, it will similarly coil around the dialysis catheter. The stripping coil 112 is advanced by rotation of the thumb wheel 144 until the stop 150 located at the proximal end 152 of the stripping coil 124 engages the capstan drive wheel 146, providing tactile feedback to the physician that the coil 124 is fully deployed.

Once the stripping coil 124 is fully deployed, the physician may slide the capstan slide lock 194 rearwardly to unlock the capstan driven wheel 148. This allows the stripping coil 124 to "float" between the capstan drive and driven wheels 146, 148.

The rotation wheel assembly 170 is then rotated clockwise (from the proximal perspective). As the spline 172 coupling the rotation wheel assembly 170 to the inner catheter 154 engage, rotation of the rotation wheel assembly 170 will cause the inner catheter 154 to rotate. Since the stripping coil 124 is essentially locked in position by the guide curve 140, it will similarly rotate as the inner catheter 154 is rotated by the rotation wheel assembly 170. This will cause a proximal-to-distal stripping action disrupting and removing the fibrin sheath from the external surface of the dialysis catheter 112.

Once the dialysis catheter 112 is clear of fibrin, the physician will reverse the procedure by sliding the capstan lock slide 194 so that it locks the capstan driven wheel 148 against the capstan drive wheel 146. The physician then rotates the stripping coil's thumb wheel 144 counterclockwise to retract the stripping coil 124. Once the fused ball 178 at the distal end 180 of the stripping coil 124 contacts the distal end of the guide curve 140, the physician is provided with tactile feedback that the stripping coil 124 is fully retracted. The capstan lock slide 194 is then released. The physician then rotates the advance/retract knob 168 180° counterclockwise to withdraw the inner catheter 154. The apparatus 110 is then unlocked from the dialysis catheter 112 and withdrawn.

With reference to FIGS. 7 to 10, an alternate embodiment of the present apparatus is disclosed. The apparatus 210 generally includes a delivery assembly 220, a stripping coil 224 formed of a shape memory material and a guide structure 222 for guiding the stripping coil 224 through the catheter 212 and to the free end 218 of the catheter 212. The stripping coil 224 is preformed to assume a shape wrapping about the exterior surface 214 of the catheter 212 in a manner providing for the stripping of build-up from the exterior surface 214 of the catheter 212 when the stripping coil 224 is moved relative to the catheter 212.

Figures 7, 8:
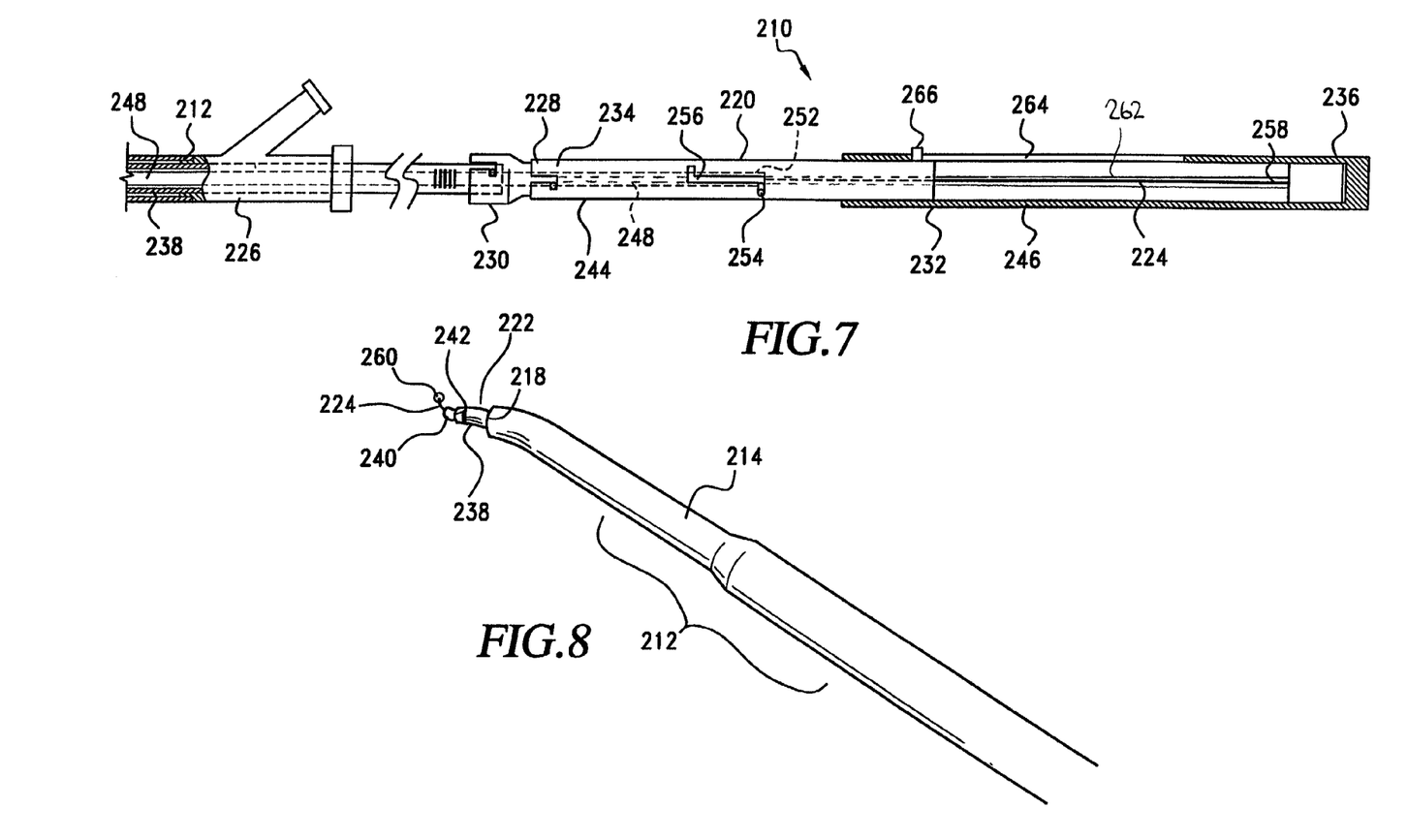
FIG. 7 is a side view of an alternate apparatus in accordance with the present invention.
FIG. 8 is a perspective view of the apparatus disclosed in FIG. 7 with the guide curve and stripping coil deployed.

With reference to FIG. 7, and in accordance with a preferred embodiment of the present invention, the delivery assembly 220 is adapted for selectively coupling to a luer connector 226 secured to the venous lumen of a traditional dialysis catheter 212. For example, and in accordance with a preferred embodiment of the present invention, the distal end 228 of the delivery assembly 220 includes a coupling member 230 shaped and dimensioned for selective attachment to a Touhy Borst Adapter, although those skilled in the art will appreciate the wide variety of connections which maybe utilized within the spirit of the present invention.

The delivery assembly 220 includes a housing 232 having a distal end 234 and a proximal end 236. As mentioned above, the proximal end 236 includes a coupling member 230. An outer catheter 238 is further secured to the proximal end 236 of the housing 232 and extends away from the housing 232 defining a lumen through which the stripping coil 224 and the guide curve 240 are passed as they are positioned adjacent the open free end 218 of the dialysis catheter 212 in a manner which will be discussed below in greater detail. With this in mind, the outer catheter 238 is shaped and dimensioned to fit within the dialysis catheter 212 and extend to approximately the open free end 218 of the dialysis catheter 212. In an effort to ensure proper positioning of the outer catheter 238 adjacent the free end 218 of the dialysis catheter 212, the outer catheter 238 is provided with radiopaque markings adjacent to its distal end 242 and printed markings adjacent its proximal end. As such, a physician may readily monitor the position of the outer catheter 238 relative to the dialysis catheter 212 (which may include radiopaque markings) so as to properly position the delivery assembly 220 before attaching the coupling member 230 to the connector 226 of the dialysis catheter 212.

The housing 232 of delivery assembly 220 further provides for the controlled storage and release of the various delivery components utilized in the proper positioning of the stripping coil 224 within the dialysis catheter 212. With this in mind, and as will be better appreciated based upon the following disclosure, the housing 232 is formed of a first housing member 244 and a second housing member 246. The first and second housing members 244, 246 are telescopically secured so that the second housing member 246 maybe slid over the first housing member 244 to move the stripping coil 224 forward within the delivery assembly 220.

An inner catheter 248 having a guide curve 240 secured at its distal end 250 is coupled within the first housing member 244. The inner catheter 248 extends within the outer catheter 238 and guides a guide curve 240 toward the distal end 242 of the outer catheter 238. In use, the guide curve 240 is moved beyond the distal end 242 of outer catheter 238 and functions to direct the stripping coil 224 as it is pushed outwardly beyond the end of the delivery assembly 220.

Movement of the guide curve 240, and the inner catheter 248, is facilitated by attaching the proximal end 252 of the inner catheter 248 to an actuation lever 254 moveably mounted within a slot 256 formed in the first housing member 244. In this way, the physician, or other individual, performing the stripping procedure simply pushes the actuation lever 254 forward within the slot 256 to move the guide curve 240 from a stored position within the outer catheter 238 to an exposed position beyond the distal end 242 of the outer catheter 238.

As mentioned above, the stripping coil 224 is coupled within the second housing member 246 of the delivery assembly 220. The stripping coil 224 includes a proximal end 258 which is coupled to the second housing member 246 of the delivery assembly 220 and a distal end 260 which generally extends through a telescoping guide tube 262 within the first and second housing members 244, 246, into the proximal end 252 of the inner catheter 248, through the inner catheter 248 and toward the guide curve 240 at the distal end 250 of the inner catheter 248. In this way, the stripping coil 224 is ready to extend beyond the inner catheter 248, outer catheter 238 and guide curve 240 such that it may freely wrap around the distal end of the dialysis catheter 212.

The distal end 260 of the stripping coil 224 is selectively moved beyond the inner catheter 248, outer catheter 238 and guide curve 240 by moving the second housing member 246 relative to the first housing member 244 in a manner which moves the stripping coil 224 forward relative to the remaining components of the present apparatus. Controlled forward movement of the second housing member 246 relative to the first housing member 244 is achieved by the provision of a slot 264 within the second housing member 246 which interacts with an abutment 266 formed on the first housing member 244.

As briefly mentioned above, the stripping coil 224 is formed from a shape memory material. In accordance with a preferred embodiment of the present invention, the stripping coil 224 is formed from a Nitinol shape memory material, although other shape memory materials may be used without departing from the spirit of the present invention.

Once the stripping apparatus 210 is fully assembled with a properly preformed stripping coil 224, the outer catheter 238 of the delivery assembly 220 is insert within the venous lumen of the dialysis catheter 212. The outer catheter 238 is passed through the dialysis catheter 212 until the distal end 242 of the outer catheter 238 extends slightly beyond the open free end 218 of the dialysis catheter 212. Controlled positioning of the outer catheter 238 and the dialysis catheter 212 is achieved by the provision of radiopaque markers on the outer catheter 238 and possibly the dialysis catheter 212.

Figure 9:
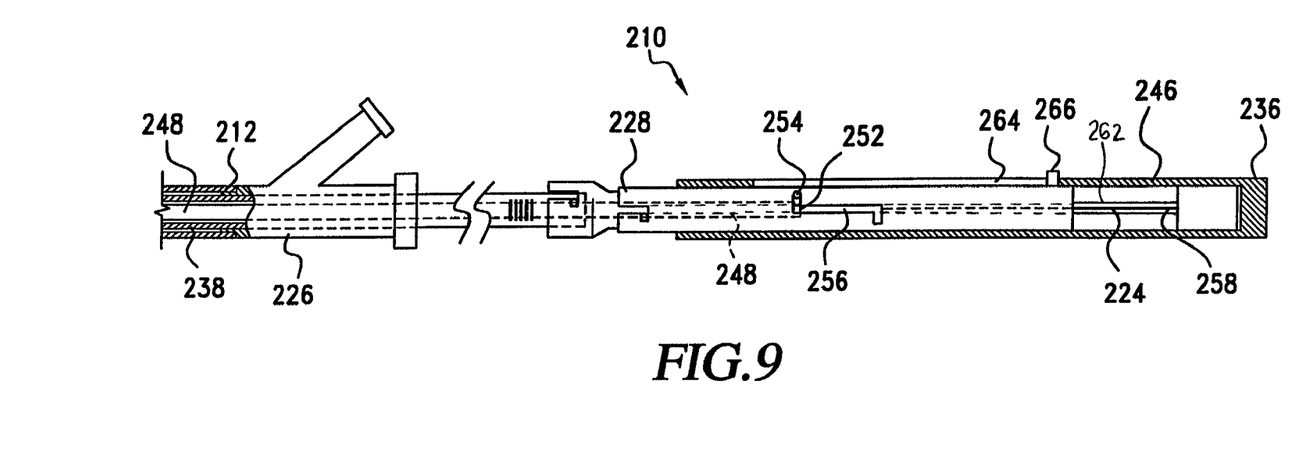
FIG. 9 is a side view of the apparatus disclosed in FIG. 7 oriented for deployment of the stripping coil.

Once the outer catheter 238 is properly positioned, the proximal end 236 of the stripping apparatus housing 232 is selectively coupled to an accessible portion of the dialysis catheter 212, for example, a connector 226 extending from the dialysis catheter 212. The guide curve actuation lever 254 is then pushed forward to move the inner catheter 248 forward and the guide curve 240 beyond the distal end 242 of the outer catheter 238. With the guide curve 240 exposed beyond the distal end 242 of the outer catheter 238, the stripping coil 224 maybe deployed.

As mentioned above, the stripping coil 224 is moved forward, beyond the other components of the present apparatus by pushing second housing member 246 forward relative to the first housing member 244. In this way, the stripping coil 224 is pushed forward and through the guide curve 240. The guide curve 240 functions to turn the stripping coil 224 around, facing it toward the dialysis catheter 212 and ensuring that the stripping coil 224 will wrap about the dialysis catheter 212 in a desired manner.

Figure 10:
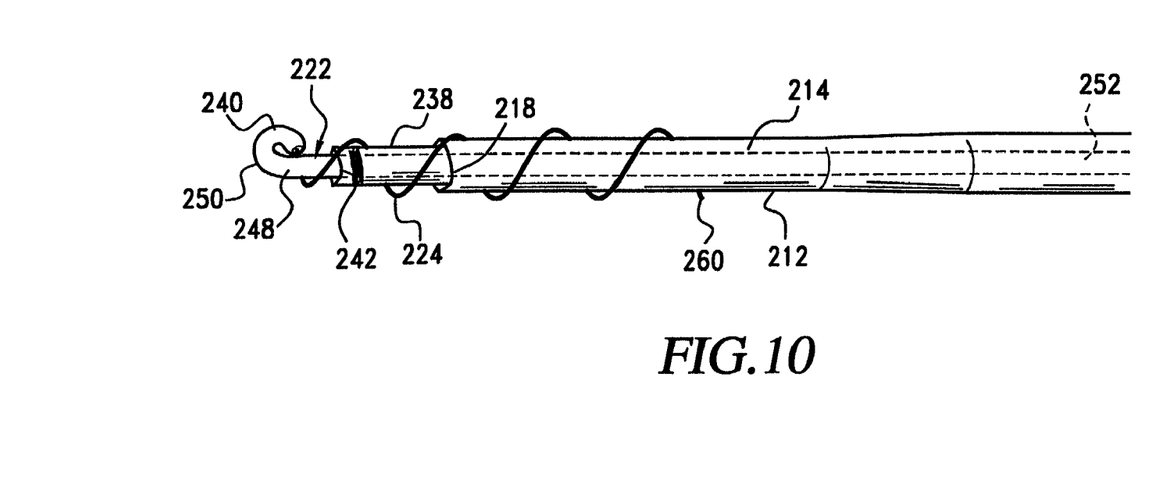
FIG. 10 is a detailed view showing the deployed stripping coil wrapped about a catheter.

Once the stripping coil 224 is guided to the distal end 242 of the outer catheter 238, and around the guide curve 240, it is released, exposing the stripping coil 224 to the elevated body temperatures. The elevated body temperatures cause the stripping coil 224 to assume the preformed, helical shape wrapping about the exterior surface 214 of the dialysis catheter 212. As discussed above, a superelastic stripping coil may also be used and will similarly wrap about the exterior surface of the dialysis catheter.

The stripping coil 224 is then rotated relative to the dialysis catheter 212 such that the stripping coil 224 disengages and removes build-up along the exterior surface 214 of the catheter 212. Rotation of the stripping coil 224 is achieved by simply rotating the delivery assembly 220.

After the fibrin build-up is fully removed from the exterior surface 214 of the catheter 212, the stripping coil 224 is drawn within the delivery assembly 220 by pulling the second housing member 244 rearwardly, the guide curve 240 and inner catheter 248 are drawn into the outer catheter 238 by pulling the actuation lever 254 rearwardly and the outer catheter 238 is withdrawn from the dialysis catheter 212.

Figure 11:
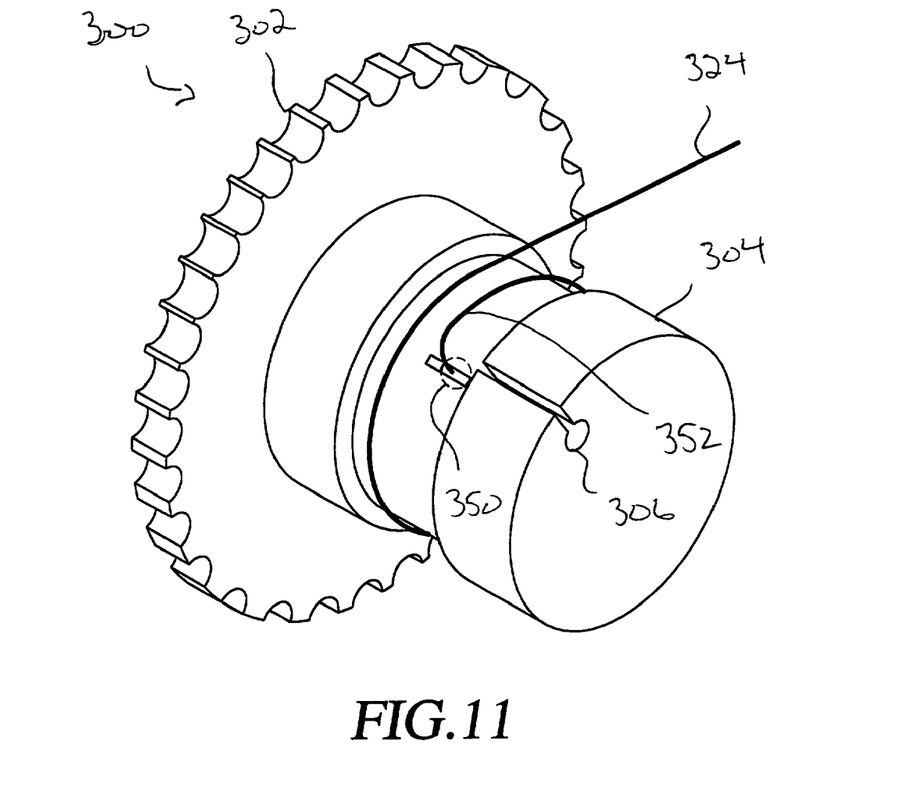
FIGS. 11 and 12 disclose an alternate drive assembly for deploying a stripping coil in accordance with the apparatus disclosed in FIG. 1.
Figure 12:
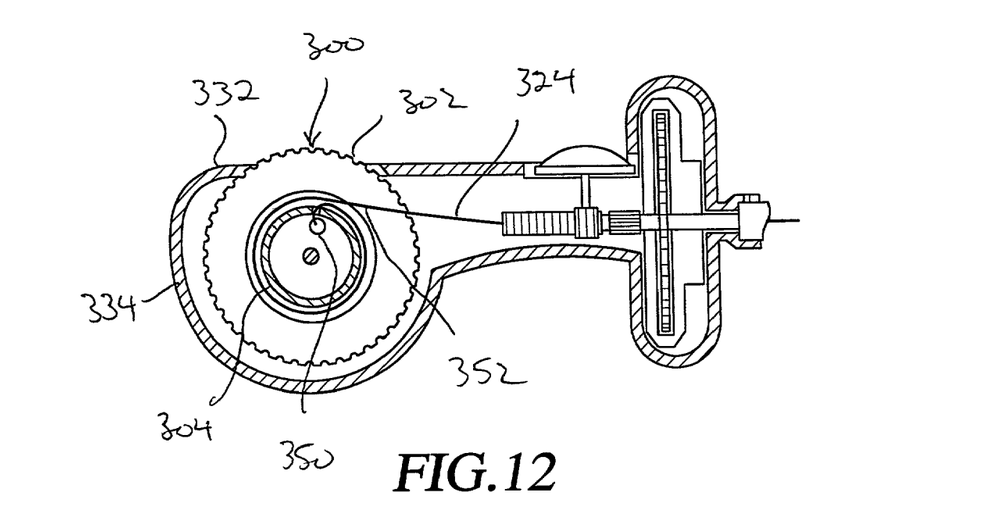

With reference to FIGS. 11 and 12, an alternate stripping coil drive assembly 300 envisioned as a replacement for the capstan drive assembly used in conjunction with the embodiment disclosed in FIGS. 1–6 is disclosed. The stripping coil drive assembly 300 is designed for positioning within the first end 334 of the housing 332. The stripping coil drive assembly 300 includes a thumb wheel 302 for engagement by a user and a spool 304 about which the stripping coil 324 may be wrapped and unwrapped as the present stripping coil drive assembly 300 is utilized. The spool 304 is provided with an engaging groove 306 into which the stop member 350 at the proximal end 352 of the stripping coil 324 is placed to securely attach the stripping coil 324 to the spool 304. In use, one simply rotates the thumb wheel 302 to selectively deploy or retrieve the stripping coil 324 in accordance with the present invention.

While the preferred embodiments have been shown and described, it will be understood that there is no intent to limit the invention by such disclosure, but rather, is intended to cover all modifications and alternate constructions falling within the spirit and scope of the invention as defined in the appended claims.

What is claimed is:

1. An apparatus for the removal of build-up about an implanted catheter having an interior surface, an exterior surface and an open free end positioned within an individual's vascular system, the apparatus comprising:
a delivery assembly storing a stripping coil, the delivery assembly including a guide structure guiding the stripping coil through the catheter to the free end of the catheter, the guide structure including a guide curve having a curved profile directing the stripping coil about the curved profile during deployment of the stripping coil;
the stripping coil being formed of a shape memory material or super elastic material, and the stripping coil including a proximal first end maintained within the delivery assembly and a free distal second end, wherein the stripping coil is preformed to assume a predetermined shape with the free distal second end wrapping about the outer surface of the catheter in a manner to provide for the stripping of build-up from the outer surface of the catheter when the stripping coil is moved relative to the catheter.

2. The apparatus according to claim 1, wherein the stripping coil is formed of Nitinol.

3. The apparatus according to claim 2, wherein the stripping coil is preformed to assume a helical shape.

4. The apparatus according to claim 3, wherein the delivery assembly includes means for rotating the stripping coil relative to the catheter so as to facilitate removal of build-up from the exterior surface of the catheter.

5. The apparatus according to claim 1, wherein the stripping coil is preformed to assume a helical shape.

6. The apparatus according to claim 5, wherein the delivery assembly includes means for rotating the stripping coil relative to the catheter so as to facilitate removal of build-up from the exterior surface of the catheter.

7. The apparatus according to claim 1, wherein the delivery assembly includes a push handle for inserting the stripping coil to the open free end of the catheter.

8. An apparatus for the removal of build-up about an implanted catheter having an interior surface, an exterior surface and an open free end positioned within an individual's vascular system, the apparatus comprising:

a delivery assembly storing a stripping coil, the delivery assembly including a guide structure guiding the stripping coil through the catheter to the free end of the catheter, the guide structure including a guide curve having a curved profile directing the stripping coil about the curved profile during deployment of the stripping coil; and the stripping coil being formed of a super-elastic material, and the stripping coil including a proximal first end maintained within the delivery assembly and a free distal second end, wherein the stripping coil is preformed to assume a shape with the free distal end wrapping about the outer surface of the catheter in a manner to provide for the stripping of build-up from the outer surface of the catheter when the stripping coil is moved relative to the catheter.

9. The apparatus according to claim 8, wherein the stripping coil is formed of Nitinol.

10. The apparatus according to claim 9, wherein the stripping coil is preformed to assume a helical shape.

11. The apparatus according to claim 10, wherein the delivery assembly includes means for rotating the stripping coil relative to the catheter so as to facilitate removal of build-up from the exterior surface of the catheter.

12. The apparatus according to claim 8, wherein the stripping coil is preformed to assume a helical shape.

13. The apparatus according to claim 12, wherein the delivery assembly includes means for rotating the stripping coil relative to the catheter so as to facilitate removal of build-up from the exterior surface of the catheter.

14. The apparatus according to claim 8, wherein the delivery assembly includes a push handle for inserting the stripping coil to the open free end of the catheter.

15. An apparatus adapted to remove build-up about an implanted catheter, comprising:

a delivery device having a stripping coil with multiple turns;

the delivery device having a stripping coil guide curve having a curved profile directing the stripping coil about the curved profile during deployment of the stripping coil;

the stripping coil being preformed of a shape memory material, and the stripping coil includes a proximal first end maintained within the delivery assembly and a free distal second end, wherein when the stripping coil is deployed from the delivery device through the stripping coil guide curve, the multiple turns of the stripping coil hug the exterior of the catheter.

16. An apparatus adapted to remove build-up about an implanted catheter, comprising:

a delivery device having a stripping coil with a free end;

the delivery device having a stripping coil guide curve having a curved profile directing the stripping coil about the curved profile during deployment of the stripping coil;

the stripping coil being preformed of a shape memory material, wherein when the stripping coil is deployed from the delivery device through the stripping coil guide curve, the stripping coil and the free end hug the exterior of the catheter.

17. An apparatus adapted to remove build-up about an implanted catheter, comprising:

a delivery assembly having a stripping coil with multiple turns and a free end, the delivery assembly including a guide structure adapted to guide the stripping coil rearwardly over an end of the catheter, the guide structure includes a guide curve having a curved profile guiding the free end of the stripping coil rearwardly as it is deployed;

the stripping coil being preformed of a super elastic material or a shape memory material, wherein when the stripping coil is deployed, multiple turns of the stripping coil hug the exterior of the catheter.

* * * * *